United States Patent
Izuhara

(10) Patent No.: US 6,711,236 B2
(45) Date of Patent: Mar. 23, 2004

(54) APERTURE POSITION ADJUSTING MECHANISM, GANTRY APPARATUS AND METHOD OF CONTROLLING IT IN X-RAY CT SYSTEM

(75) Inventor: Akira Izuhara, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 14 days.

(21) Appl. No.: 10/202,149

(22) Filed: Jul. 23, 2002

(65) Prior Publication Data

US 2003/0021385 A1 Jan. 30, 2003

(30) Foreign Application Priority Data

Jul. 25, 2001 (JP) ........................................ 2001-224725

(51) Int. Cl.[7] ................................................ G21K 1/04
(52) U.S. Cl. ..................... 378/151; 378/150; 378/205; 378/207; 250/505.1
(58) Field of Search ................................ 378/147, 150, 378/151, 152, 205, 207; 250/505.1

(56) References Cited

U.S. PATENT DOCUMENTS

| | | | | |
|---|---|---|---|---|
| 4,361,764 A | * | 11/1982 | Zieler ........................... | 378/14 |
| 4,361,902 A | | 11/1982 | Brandt et al. ................ | 378/152 |
| 4,476,569 A | * | 10/1984 | Ogo ............................ | 378/175 |
| 4,868,843 A | | 9/1989 | Nunan ........................ | 378/152 |
| 4,991,189 A | | 2/1991 | Boomgaarden et al. ........ | 378/4 |
| 5,090,037 A | | 2/1992 | Toth et al. ..................... | 378/4 |
| 5,396,534 A | * | 3/1995 | Thomas ........................ | 378/160 |
| 5,583,903 A | * | 12/1996 | Saito et al. ................... | 378/19 |
| 5,644,614 A | | 7/1997 | Toth et al. ................... | 378/147 |
| 5,684,855 A | * | 11/1997 | Aradate et al. ................. | 378/4 |
| 5,949,811 A | | 9/1999 | Baba et al. ................. | 378/108 |
| 5,949,843 A | * | 9/1999 | Tamaki et al. ................. | 378/17 |
| 5,970,112 A | | 10/1999 | Hsieh ............................. | 378/8 |
| 5,982,846 A | | 11/1999 | Toth et al. ..................... | 378/19 |
| 6,056,437 A | | 5/2000 | Toth ............................ | 378/205 |
| 6,061,419 A | | 5/2000 | Hsieh et al. .................... | 378/4 |
| 6,173,039 B1 | | 1/2001 | Hampel et al. ............. | 378/150 |
| 6,298,117 B1 | | 10/2001 | Hampel et al. ............. | 378/150 |
| 6,301,334 B1 | * | 10/2001 | Tybinkowski et al. ...... | 378/147 |
| 6,507,642 B2 | * | 1/2003 | Fujishige et al. ........... | 378/151 |

* cited by examiner

Primary Examiner—Edward J. Glick
Assistant Examiner—Allen C Ho
(74) Attorney, Agent, or Firm—Carl B. Horton, Esq.; Armstrong Teasdale LLP

(57) ABSTRACT

In order to provide an aperture position adjusting mechanism in an X-ray CT system with low cost and high accuracy to enable stable reconstruction of X-ray tomographic images, a first shaft (23) is provided with a bore (23a) at a position offset from a center axis, and is rotatably supported by a base plate (20) orthogonally to a pair of rails (21a, 21b). A second shaft (25) is received and is rotatably supported within the bore (23a) through the first shaft (23). The aperture (6) is moved along the rails (21a, 21b) as the second shaft (25) is eccentrically rotated by a motor (7) and, following the eccentric rotation and in a direction opposite to that of the rotation, the first shaft (23) is eccentrically rotated around the center axis of the bore (23a).

6 Claims, 8 Drawing Sheets

US 6,711,236 B2

APERTURE POSITION ADJUSTING MECHANISM, GANTRY APPARATUS AND METHOD OF CONTROLLING IT IN X-RAY CT SYSTEM

CROSS REFERENCE TO RELATED APPLICATIONS

This application claims the benefit of Japanese Application No. 2001-224725 filed Jul. 25, 2001.

BACKBROUND OF THE INVENTION

The present invention relates to an aperture position adjusting mechanism, a gantry apparatus and a method of controlling it in an X-ray CT (computerized tomography) system for obtaining an X-ray tomographic image of a subject by X-ray irradiation.

An X-ray CT system is mainly directed to the purpose of collecting projection data obtained from X-rays passing through a subject, and reconstructing an X-ray tomographic image from the projection data. Specifically, the following steps are taken: the subject is first laid on a table apparatus, and is carried to a cavity portion in a gantry apparatus. A rotating section (to which an X-ray tube and an X-ray detector are integrally attached) in the gantry apparatus is then rotated, X-rays are directed to the subject from different angles, and X-rays passing through the subject are detected at these angles. The detected data (projection data) is then received by an operating console, and an X-ray tomographic image is reconstructed by arithmetic operations. The sequence of steps for detecting X-rays as described above is generally referred to as a scan.

Also known is what is commonly referred to as a multi-slice X-ray CT system, in which the X-ray detecting section is comprised of a detector array comprising a plurality of rows arranged in the carrying direction of the table, enabling collection of data for a plurality of slices in one scan. The multi-slice X-ray CT system has an advantage that a plurality of X-ray tomographic images can be obtained in one scan.

It is generally known that during such a scan, heat gradually accumulated with the generation of X-rays from the X-ray tube leads to a shift of the focal position of the X-ray tube in the carrying direction of the table (which will be sometimes referred to as a z-axis hereinbelow). This point will be explained below.

FIG. 7 is a schematic diagram of the focal point of an X-ray tube, an aperture and an X-ray detector (comprised of two detector rows A, B) as viewed from a direction orthogonal to the z-axis.

In the drawing, the focal point is initially at a position indicated by a solid line. At this time, the position of the aperture in the z-direction is controlled so that the X-rays impinge equally on the detector rows A and B. In such an environment, the focal point shifts in the z-axis direction as indicated by a broken line by actually driving the gantry apparatus. If the position of the aperture remains at the illustrated position, the X-ray irradiation range in the z-axis direction shifts to a range indicated by broken lines. As can be seen from FIG. 7, the X-rays no longer impinge upon the overall surface of the detector row A in such a condition, and consequently, the relationship between signals a and b output from the respective detector rows becomes a<b, resulting in different CT values (pixel values in an X-ray tomographic image) to be reconstructed and different imaging ranges (thicknesses) between the detector rows.

Accordingly, a general X-ray CT system comprising a plurality of detector rows (multi-slice X-ray CT system) comprises a mechanism that employs detector elements typically at the ends among detector elements (also referred to as detector channels) as reference channels, determines that the focal point is shifted when the outputs from the reference channels are unequal between the rows, and adjusts the position of the aperture in the z-direction so that the outputs are equalized. Such a mechanism enables X-rays to constantly impinge equally upon all the detector rows.

FIG. 8 is a prior art mechanism for conducting such aperture position adjustment. The hatched portion on a component in the drawing indicates that the mechanism is mounted on a certain base within the rotating section in the gantry apparatus.

As shown, an aperture 80 is provided with a slit 80a for defining the X-ray irradiation range, and is supported by an aperture base plate 81. A pair of parallel translating rails 82a and 82b are disposed along the z-axis direction, and the aperture base plate is slidably supported by the translating rails 82a and 82b via linear guides 83a and 83b formed at opposite ends of the aperture base plate. Moreover, a ball screw 84 is provided alongside of the translating rail 82a in parallel, and is attached to an output shank of a motor 86 via a coupling 85. Finally, a nut 87 fitted on the ball screw 84 is fixed to the linear guide 83a, as shown.

A rotational motion of the ball screw 84 conducted by the driving motor 87 is transformed into a linear motion of the nut 87. Since the nut 87 is fixed to the linear guide 83a, the aperture base plate 81 is moved following the linear guide 83a along the translating rails 82a and 82b (i.e., along the z-axis direction). The position adjustment of the aperture 80 is thus achieved.

In the aperture position adjustment, accuracy of the order of several micrometers is required, and therefore, the effect of backlash between the ball screw and nut needs to be eliminated as much as possible.

In the conventional case as described above, however, since the ball screw 84 is attached to an end side of the aperture base plate 81, the backlash contained in the ball screw 84 and elastic deformation of the ball screw 84 may cause an inclination of the aperture 80, leading to a problem that desired accuracy may not be attained.

The ball screw cannot be disposed in the center of the aperture to overcome this problem, however, because this is where the X-ray beam passes.

Alternatively, it can be contemplated that ball screws are disposed at opposite ends of the aperture base plate to reduce the effect of backlash; however, other problems arise that this increases the cost, and the two ball screws should be strictly adjusted during assembling.

SUMMARY OF THE INVENTION

Therefore, an object of the present invention is to provide an aperture position adjusting mechanism in an X-ray CT system with low cost and high accuracy, and to provide a gantry apparatus and a method of controlling it that enable stable reconstruction of X-ray tomographic images.

According to the present invention, there is provided an aperture position adjusting mechanism in an X-ray CT system capable of adjusting the position of an aperture (6) having an aperture opening for limiting an X-ray irradiation range, comprising: a pair of rails (21a, 21b) disposed along a direction in which said aperture (6) is to be adjusted, for slidably mounting said aperture (6); a first shaft (23) that is hollow and is provided with a bore (23a) passing in parallel with a center axis of said first shaft (23) at a position offset from said center axis, said first shaft (23) being rotatably supported by a base portion (20) of said aperture (6) orthogonally to said pair of rails (21a, 21b); a second shaft (25) that is received and is rotatably supported within said bore (23a) of said first shaft (23); and driving means (7) for rotating said second shaft (25) in reciprocal directions around an eccentric axis offset from a center axis of said second shaft (25), said mechanism characterized in that: said aperture (6) is moved along said rails (21a, 21b) as said second shaft (25) is eccentrically rotated by said driving means (7) and, following said eccentric rotation and in a direction opposite to that of said rotation, said first shaft (23) is eccentrically rotated around a center axis of said bore (23a).

Moreover, according to the present invention, there is provided a gantry apparatus in an X-ray system, comprising an aperture position adjusting mechanism.

The gantry apparatus preferably comprises an X-ray detecting section in which a plurality of detector rows are arranged in a carrying direction of a table for carrying a subject, each of said detector rows having a group of detector elements arranged in a direction orthogonal to said carrying direction; and the direction in which said aperture is to be adjusted preferably coincides with said carrying direction.

Moreover, the gantry apparatus preferably further comprises control means for feedback-controlling said driving means so that outputs from detector elements at a predefined position in said detector rows are equalized when the focal position of an X-ray source shifts.

According to the present invention, there is also provided a method of controlling a gantry apparatus in an X-ray CT system comprising: a gantry rotating section for integrally rotating an X-ray detecting section and an X-ray source, said X-ray detecting section comprising a plurality of detector rows arranged in a carrying direction of a table for carrying a subject, each of said detector rows having a group of detector elements arranged in a direction orthogonal to said carrying direction, said X-ray source disposed at a position opposite to said X-ray detecting section across a cavity portion for inserting said table; an aperture having an aperture opening for limiting an irradiation range of X-rays from said X-ray source; and adjusting means for adjusting the position of said aperture in said carrying direction, said adjusting means comprising: a pair of rails disposed along a direction in which said aperture is to be adjusted, for slidably mounting said aperture; a first shaft that is hollow and is provided with a bore passing in parallel with a center axis of said first shaft at a position offset from said center axis, said first shaft being rotatably supported by a base portion of said aperture orthogonally to said pair of rails; a second shaft that is received and is rotatably supported within said bore of said first shaft; and driving means for rotating said second shaft in reciprocal directions around an eccentric axis offset from a center axis of said second shaft, said method characterized in comprising: a scanning step for performing a scan for collecting X-ray projection data of the subject during a rotation of said gantry rotating section; and a control step for feedback-controlling said driving means so that outputs from detector elements at a predefined position in said detector rows are equalized when the focal position of the X-ray source shifts during the rotation of said gantry rotating section.

The present invention can provide an aperture position adjusting mechanism in an X-ray CT system with low cost and high accuracy, and can provide a gantry apparatus and a method of controlling it that enable stable reconstruction of X-ray tomographic images.

DETAILED DESCRIPTION OF THE INVENTION

Embodiments will now be described in detail with reference to the accompanying drawings.

Figure 1:
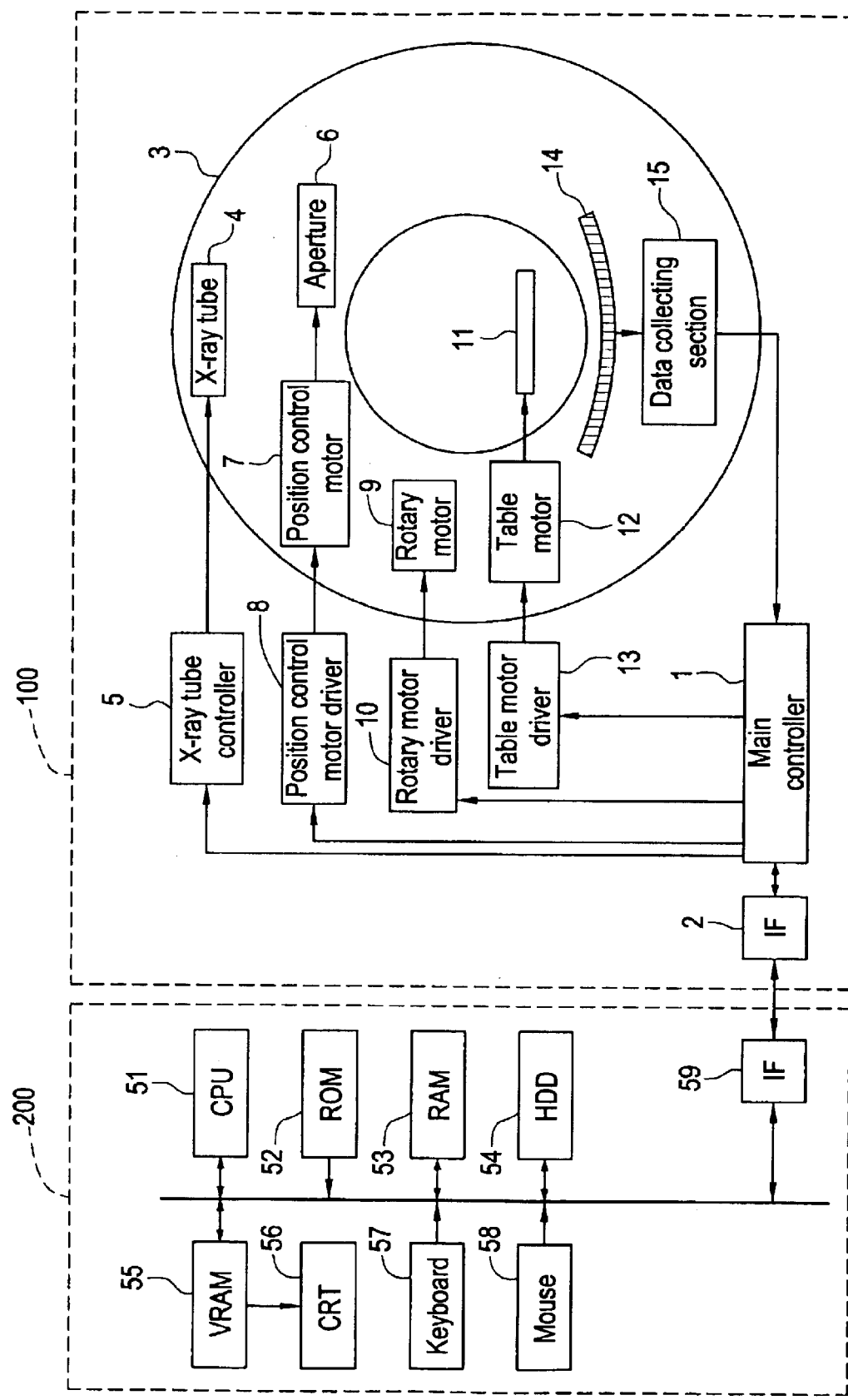
FIG. 1 is a block configuration diagram of an X-ray CT system in accordance with an embodiment.

FIG. 1 is a block configuration diagram of an X-ray CT system in accordance with an embodiment. As shown, the system is comprised of a gantry apparatus 100 for irradiating a subject with X-rays and detecting X-rays passing through the subject, and an operating console 200 for performing several kinds of operating settings for the gantry apparatus 100, and reconstructing an X-ray tomographic image based on data output from the gantry apparatus 100 for display.

The gantry apparatus 100 comprises a main controller 1 for controlling the entire apparatus 100, and the components discussed in the following.

Reference numeral 2 designates an interface for communicating with the operating console 200, and 3 designates a gantry having a cavity portion for carrying a subject (patient) laid on a table 11 (in a direction perpendicular to the drawing plane, which direction will be referred to as a z-axis hereinbelow, and which generally coincides with a body axis of the patient). Reference numeral 4 designates an X-ray tube which is an X-ray generating source, and is driven and controlled by an X-ray tube controller 5.

Reference numeral 6 designates an aperture having an aperture opening for limiting the X-ray irradiation range, 7 designates a position control motor for adjusting the position of the aperture 6 in the z-axis direction, and 8 designates a position control motor driver for driving and controlling the position control motor 7.

A mechanism for controlling the position of the aperture 6 described above will be explained in detail later.

Reference numeral 9 designates a rotary motor for rotating the gantry 3, and 10 designates a rotary motor driver for driving the rotary motor 9. Reference numeral 11 designates a table for resting the subject, 12 a table motor for carrying the table 11 in the z-axis direction, and 13 a table motor driver for driving and controlling the table motor 12.

Reference numeral 14 designates an X-ray detecting section for detecting X-rays from the X-ray tube 4 passing through the aperture 6 and the cavity portion within the gantry 3, which here comprises two detector rows arranged in the z-axis direction. However, the present invention does not limit the number of rows, and, for example, four or eight detector rows may be contemplated. Each detector row has a plurality of (e.g., 1,000) detector channels over a length depending upon the X-ray irradiation range defined by the aperture 6. The detector channel at an end of each row is directly exposed to an X-ray beam not passing through the subject, and is used as a reference channel. Reference numeral 15 designates a data collecting section for collecting projection data obtained by the X-ray detecting section 14 and converting the projection data into digital data.

The operating console 200 is what is commonly referred to as a workstation, comprising a CPU 51 for controlling the entire apparatus, a ROM 52 storing a boot program etc., a RAM 53 that serves as a main storage device, as shown, and the following components.

An HDD 54 is a hard disk device, which stores an OS and a diagnosis program for supplying several kinds of instructions to the gantry apparatus 100 and reconstructing an X-ray tomographic image based on data received from the gantry apparatus 100. A VRAM 55 is a memory for developing image data to be displayed, and the image data can be displayed on a CRT 56 by developing the image data and the like there. Reference numerals 57 and 58 designate a keyboard and a mouse for performing several kinds of settings. Reference numeral 59 designates an interface for communicating with the gantry apparatus 100.

The configuration of the X-ray CT system in the embodiment is generally as described above. In the X-ray CT system having such a configuration, collection of projection data is conducted as follows.

First, an operator (technician or physician) operates the operating console to prescribe several scan conditions, and then, gives a scan start instruction. A diagnosis program running on the operating console in turn issues several control commands to the gantry apparatus 100 (main controller 1) according to the prescribed scan conditions. The main controller 1 in the gantry apparatus 100 supplies control signals to the X-ray tube controller 5, position control motor driver 8, rotary motor driver 10 and table motor driver 13 according to the control commands. Consequently, X-rays generated at the X-ray tube 4 and passing through the subject can be detected by the X-ray detecting section 14, and the projection data of the X-rays can be obtained from the data collecting section 15.

Particularly, the following operations are repeated: the gantry 3 is rotated one time with carrying of the table 11 stopped, and in the meantime, an X-ray beam is emitted from the X-ray tube 4 toward the subject (i.e., X-rays are projected) from a plurality of (e.g., 1,000) view directions over 360° and the transmitted X-rays are detected by the X-ray detecting section 14. The detected transmitted X-rays are converted into digital values at the data collecting section 15, and are transferred as projection data to the operating console 200 via the main controller 1. Such a unitary sequence of operations is referred to as one scan. Then the scan position is sequentially moved in the z-axis direction by a predetermined amount to perform a next scan. Such a scan scheme is referred to an axial scan scheme. It should be however noted that the scan scheme may be a helical scan scheme involving collecting the projection data while continuously moving the table 11 synchronously with the rotation of the gantry 3 (in which scheme the X-ray tube 4 and the X-ray detecting section 14 are helically rotated around the subject).

The diagnosis program, running on the operating console 200 performs processing to reconstruct an X-ray tomographic image by a known processing method based on the transferred projection data, and sequentially displays the results of the reconstruction on the CRT 56.

As described earlier, the X-ray detecting section 14 in the embodiment comprises two detector rows A and B arranged in the z-axis direction to achieve multi-slice X-ray CT. In other words, projection data for two slices can be collected in one scan. It will be easily recognized that the projection data for two slices may be combined to provide an X-ray tomographic image having a slice thickness corresponding to the width of two detector rows.

Moreover, a mechanism is provided for determining that the focal point of the X-ray tube 4 shifts when the outputs from the reference channels are unequal between the detector rows in the X-ray detecting section 14, and adjusting the position of the aperture 6 in the z-axis direction by feedback control so that the outputs are equalized. Thus, X-rays constantly impinge equally upon the two detector rows.

A conventional mechanism for performing such aperture position adjustment is configured to drive a ball screw disposed in the proximity of one end of an aperture base plate, as described earlier, and such a conventional mechanism has a problem of accuracy due to backlash contained in the ball screw and elastic deformation of the ball screw 84.

The inventors successfully realized a position adjusting mechanism with higher accuracy by employing a structure having combined eccentric axes instead of the ball screw.

Figure 2:
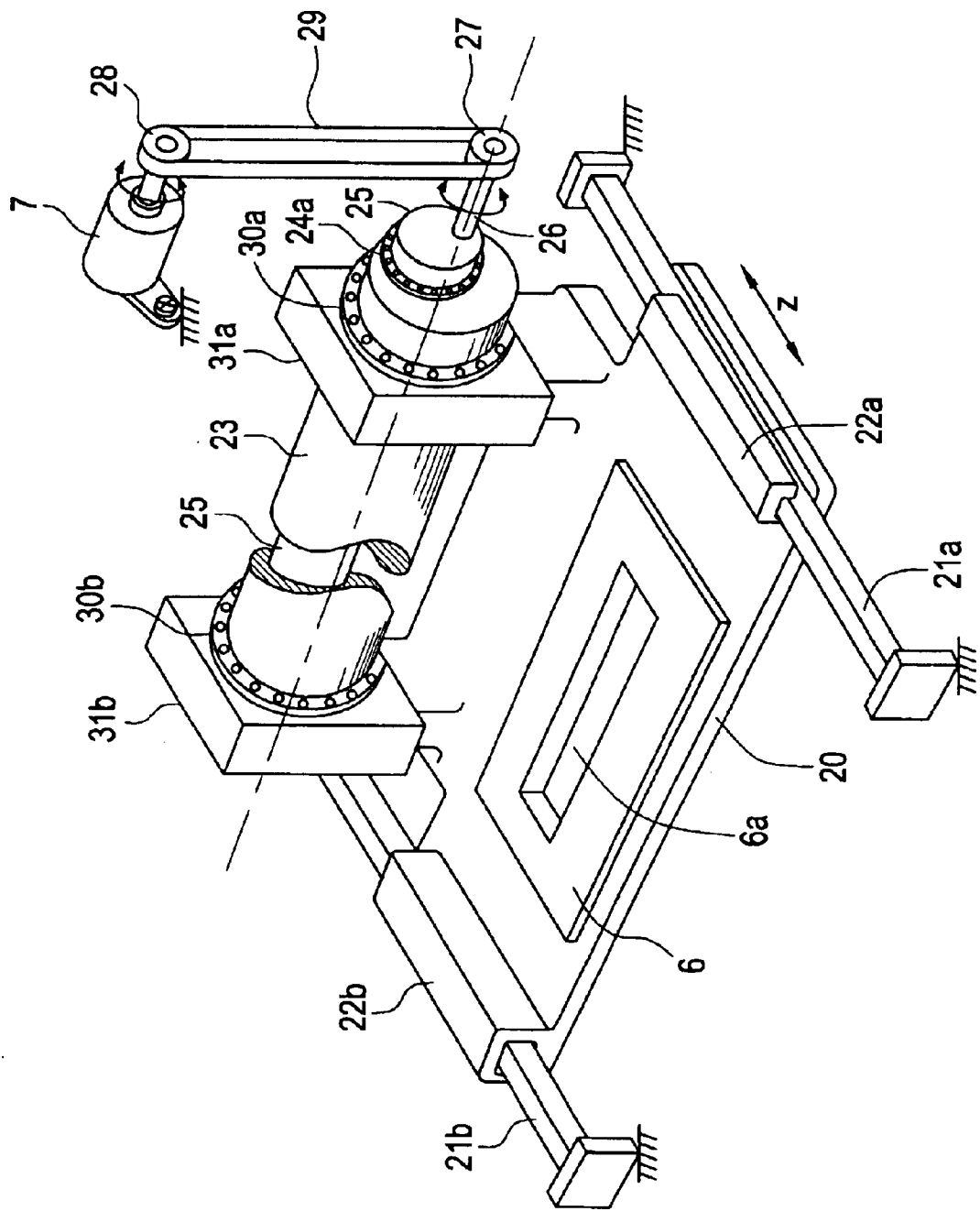
FIG. 2 is a view for explaining an aperture position adjusting mechanism in the embodiment.
Figure 3:
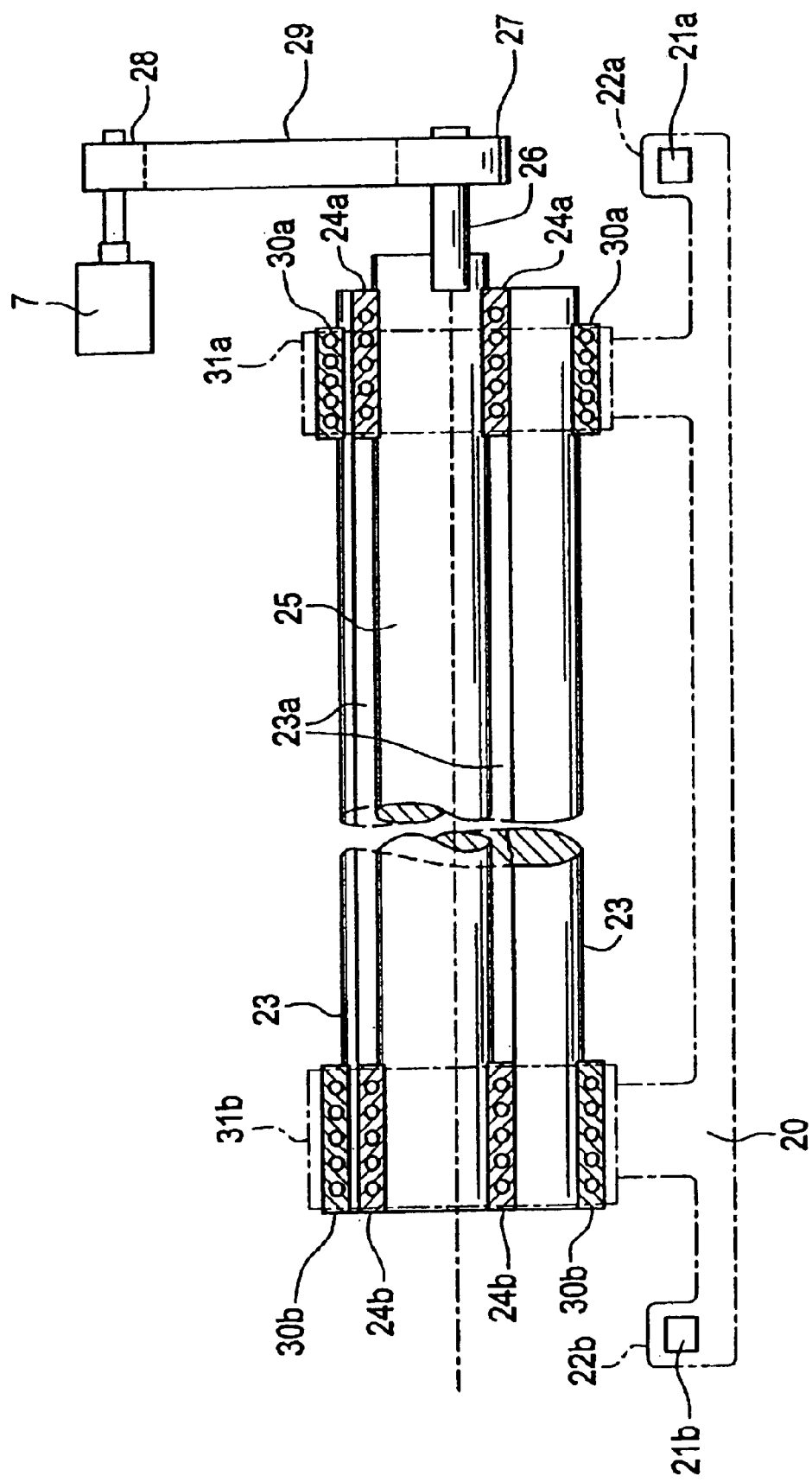
FIG. 3 is a view for explaining the aperture position adjusting mechanism in the embodiment.

An aperture position adjusting mechanism in the embodiment of the present invention is shown in FIGS. 2 and 3. FIG. 2 is an external perspective view, and FIG. 3 is a front elevational view (partially a cross-sectional view). The hatched portion on a component in the drawing indicates that the mechanism is mounted on a certain base within the gantry 3.

As shown, the aperture 6 is provided with a slit 6a for defining the X-ray irradiation range, and is supported by an aperture base plate 20. A pair of parallel translating rails 21a and 21b are disposed along the z-axis direction, and the aperture base plate 20 is slidably supported by the translating rails 21a and 21b via linear guides 22a and 22b formed at opposite ends of the aperture base plate 20. Thus, the position of the aperture 6 can be adjusted by the aperture base plate 20 moving along the translating rails 21a and 21b.

The mechanical section for moving the aperture base plate 20 in the embodiment is positioned on one end in the z-axis direction (i.e., at the rear of the aperture 6), differently from the conventional mechanism.

First, a large-diameter shaft 23 is a first axial member that is hollow and is provided with a bore 23a passing in parallel with a center axis of the large-diameter shaft 23 at a position offset from the center axis by a predetermined amount (at an off-centered position). The inner periphery of the bore 23a of the large-diameter shaft 23 is fitted with first bearings 24a and 24b at opposite ends. A small-diameter shaft 25 is inserted into the large-diameter shaft 23 along the bore 23a, and is rotatably supported by the first bearings 24a and 24b. Moreover, on a surface at one end of the small-diameter shaft 25, a bore provided at a position offset from a center axis of the small-diameter shaft 25 by a predetermined amount (at an off-centered position) is locked to a basis axial member 26, and thus the center axis of the small-diameter shaft 25 and the center axis of the basis axial member 26 are fixed in parallel. The other end of the basis axial member 26 is attached with a pulley 27, and a belt 29 is stretched around the pulley 27 and a pulley 28 that is attached to an output shank of the reciprocally acting position control motor 7. Thus, by driving the position control motor 7, the basis axial member 26 rotates around its basis axis via the belt 29.

The outer periphery of the large-diameter shaft 23 is fitted with second bearings 30a and 30b at opposite ends of the shaft 23, and the bearings 30a and 30b are confined within respective housings 31a and 31b. The housings 31a and 31b are in turn fixed to one end of the aperture base plate 20 in the z-axis direction so that the large-diameter shaft 23 is orthogonal to the translating rails 21a and 21b.

Although the two bearings 30a and 30b (and the housings 31a and 31b) are configured to support opposite ends of the large-diameter shaft 23 in the drawings, such a configuration is only one example, and the large-diameter shaft 23 may be supported by, for example, constructing one bearing and one housing having a width covering generally the whole of the large-diameter shaft 23.

In the aforementioned configuration, how the aperture base plate 20 is moved in the z-axis direction will now be described with reference to a schematic side view with respect to the housing 31a shown in FIG. 4.

Figure 4A:
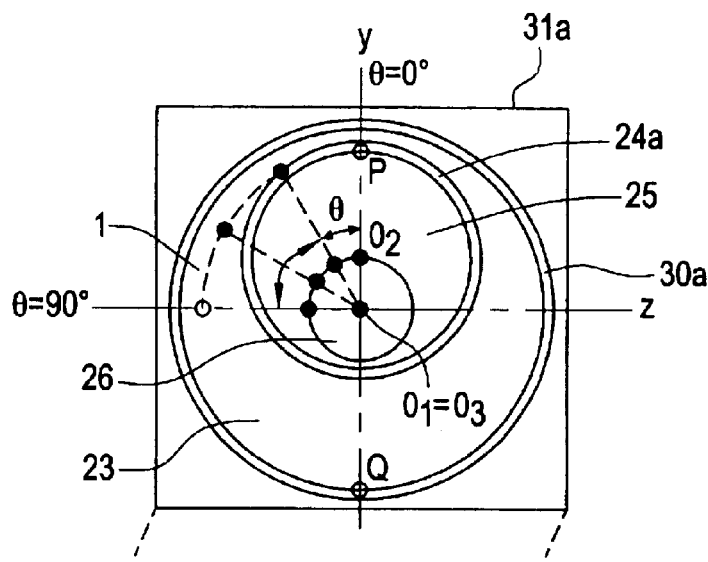
FIG. 4 is a schematic diagram for explaining the operation of the aperture position adjusting mechanism in the embodiment.

In FIG. 4(a), reference symbol $O_1$ is a basis axis, i.e., a center of rotation of the basis axial member 26. $O_1$ is also a center of rotation of the small-diameter shaft 25. That is, the small-diameter shaft 25 acts as an eccentric cam with a center of rotation of $O_1$. Reference symbol $O_2$ is a center of rotation of a first bearing 24a. Therefore, the offset of the small-diameter shaft 25 as an eccentric cam is a distance $O_1O_2$. When a point on the outer periphery of the small-diameter shaft 25 that lies at a maximum distance from $O_1$ is represented as P, a straight line $O_1P$ passes through $O_2$.

For convenience of explanation, a z-y coordinate system is defined with an origin $O_1$. In (a), $O_2$ lies just above $O_1$ (i.e., on the y-axis), and hence P also lies just above $O_1$ (i.e., on the y-axis), as shown. At this time, a center of rotation $O_3$ of the second bearing 30a is assumed to coincide with $O_1$.

Moreover, $O_2$ is the center of rotation of the first bearing 24a as pointed out above, and it is also a center of rotation of the large-diameter shaft 23. That is, the large-diameter shaft 23 acts as an eccentric cam with a center of rotation of $O_2$. Therefore, an offset of the large-diameter shaft 23 as an eccentric cam is a distance $O_3O_2$. When a point on the outer periphery of the large-diameter shaft 23 that lies at a maximum distance from $O_2$ is represented as Q, a straight line $O_2Q$ passes through $O_3$, and Q lies on the y-axis in the condition of (a).

In the embodiment, the point P can be moved within a second quadrant in the z-y coordinate system by rotating the basis axial member 26 counterclockwise with respect to the drawing plane by driving the position control motor 7. In other words, when an angle formed between the straight line $O_3P$ and the y-axis is represented as θ as shown, the point P can move within a range 0°<θ<90°. In FIG. 4, a broken line l shows a trajectory of movement of P in this case.

Rotation of the small-diameter shaft 25 starting with P lying near the y-axis gives a slope to the straight line $O_1P$. At the same time, the center of rotation $O_2$ of the first bearing 24a lying on the straight line $O_1P$ moves to the left with the slope and its height position is gradually lowered. That is, the position of the first bearing 24a itself moves to the lower left by the action of the small-diameter shaft 25 as an eccentric cam.

Figure 4B:
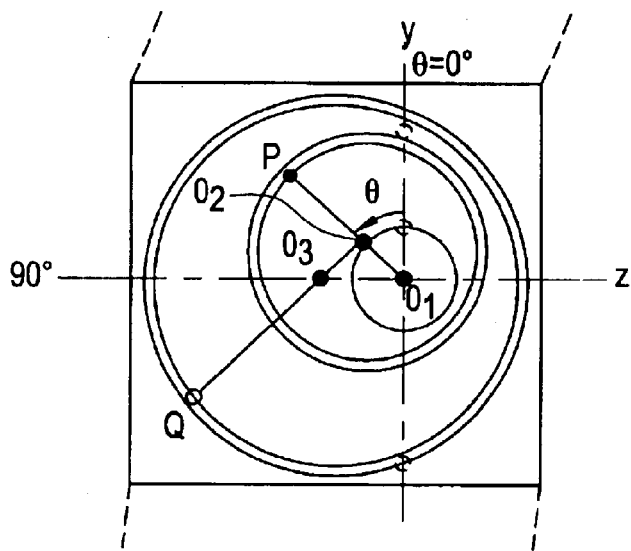
Figure 4C:
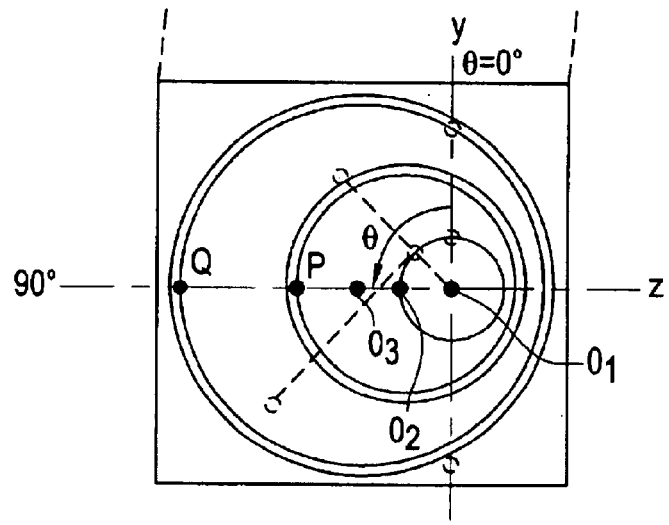

However, since the housing 31a itself is fixed to the aperture base plate 20, movement in the height direction is restricted. Therefore, as the first bearing 24a moves to the lower left, the large-diameter shaft 23 rotates around $O_2$ in a direction opposite to the rotation direction of the small-diameter shaft 25 so that the movement of the first bearing 24a to the lower side is cancelled out. In other words, the rotation of the small-diameter shaft 25 moves the center of rotation $O_2$ of the first bearing 24a to the lower left, and the straight line $O_2Q$ approaches horizontal by the inverse rotation of the large-diameter shaft 23 following the rotation of the small-diameter shaft 25. At the same time, the rotation center line $O_3$ of the second bearing 30a lying on the straight line $O_2Q$ moves to the left on the z-axis direction. That is, the position of the second bearing 30a itself moves to the left by the action of the larger-diameter shaft 23 as an eccentric cam. Therefore, following the movement of $O_3$, the aperture base plate 20 fixed to the housing 31a is moved along the rail 21a. FIG. 4(b) shows a condition where θ is 45°, and (c) shows a condition where θ is approximately 90°.

By the mechanism as described above, the position of the aperture 6 in the z-axis direction can be adjusted. It will be easily recognized that when the position control motor 7 is inversely driven to rotate the basis axial member 26 clockwise with respect to the drawing plane, the aperture base plate is moved in the opposite direction by an action completely inverse to that described above.

Figure 5:
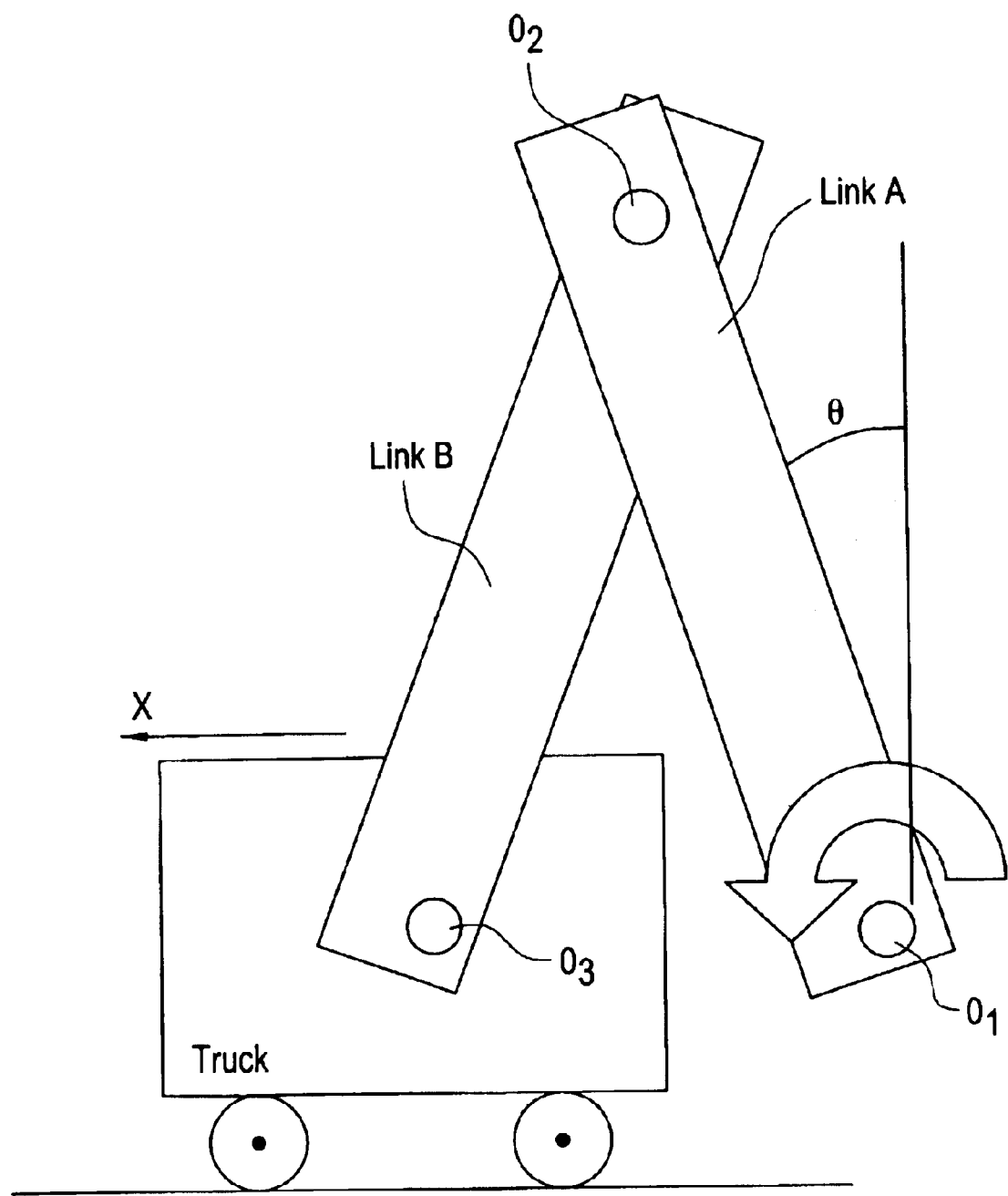
FIG. 5 shows a link mechanism corresponding to the aperture position adjusting mechanism in the embodiment.

Now consider the motion of $O_2$ and $O_3$ with respect to $O_1$. The trajectory of $O_2$ is an arc around $O_1$. On the other hand, $O_3$ moves on the z-axis following the motion of $O_2$. Such motion corresponds to motion of a link mechanism (slider-crank mechanism) shown in FIG. 5. Specifically, the straight line $O_1O_2$ corresponds to a link A, and the straight line $O_2O_3$ corresponds to a link B, and $O_3$ moving along the x-axis corresponds to movement of a truck.

According to the present invention, however, since the small-diameter shaft 25 and large-diameter shaft 23 serving as two eccentric cams are integrated to have a length capable of transmitting a driving force to the housings 31a and 31b at opposite ends at the same time, as described above, the mechanism itself can be reduced in size, and in addition, a great advantage can be offered that play likely to occur in a common link mechanism can be reduced and rigidity can be improved.

Moreover, the large-diameter shaft 23 is a hollow shank that can be manufactured by processing involving only drilling a bore offset from the central axis, and the small-diameter shaft 25 can also be manufactured only by drilling a bore sufficient to fix the basis axial member 26 at a position offset from the center axis. Furthermore, since other components only include ball bearings, the mechanism can be embodied with low cost.

Considering controllability, the eccentric offsets of the small-diameter shaft 25 and large-diameter shaft 23 and the positional relationship between them are preferably set so that $$O_1O_2=O_2O_3,$$

and $$\angle O_2O_1O_3=\angle O_2O_3O_1.$$

However, the present invention is not limited to such a condition.

Figure 6:
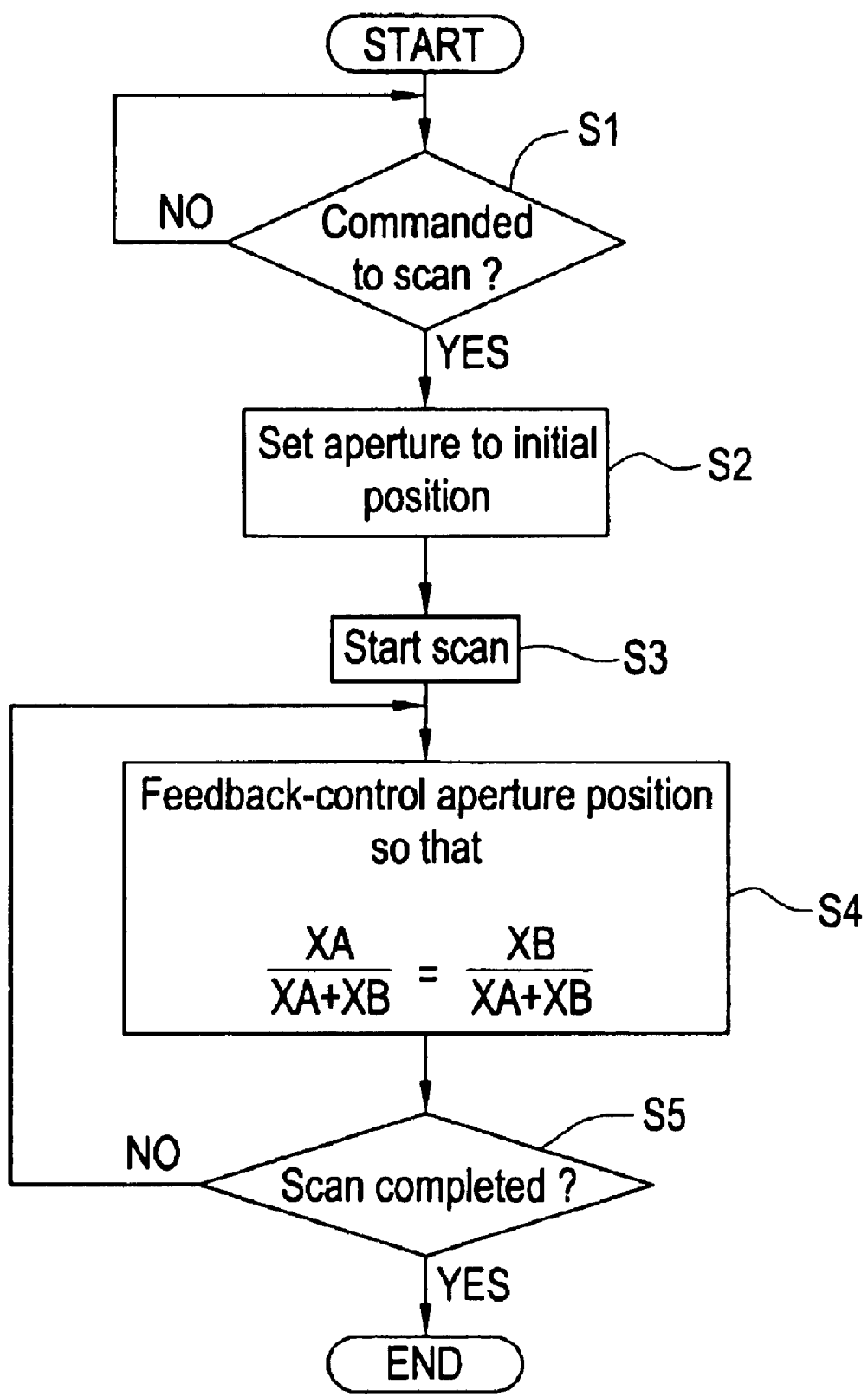
FIG. 6 is a flow chart showing aperture movement control processing following movement of the focal point of an X-ray tube in the embodiment.
Figure 7:
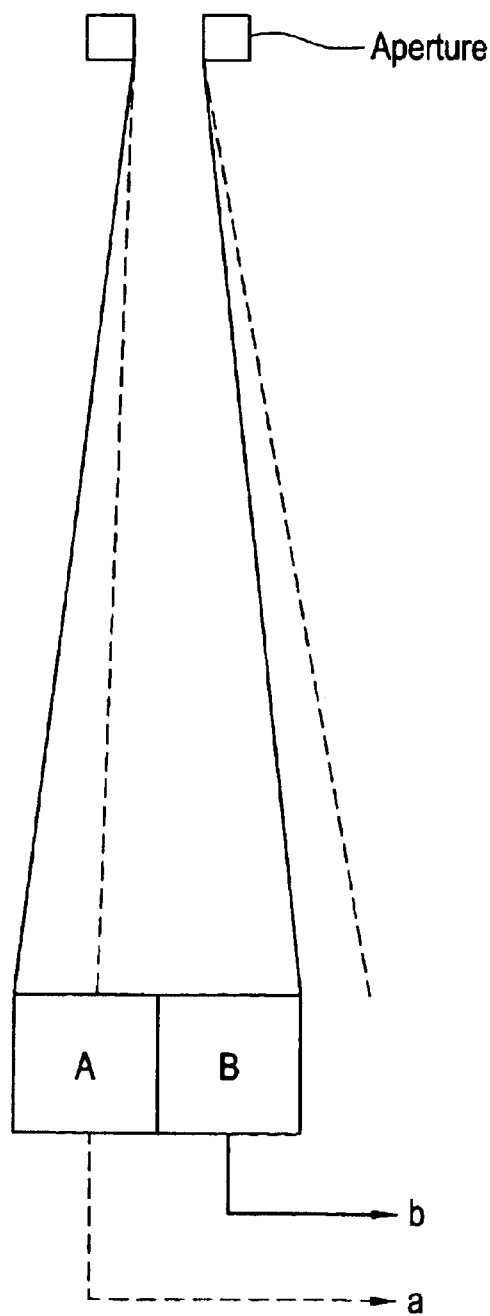
FIG. 7 is a diagram for explaining a phenomenon involved in movement of the X-ray tube focal point.
Figure 8:
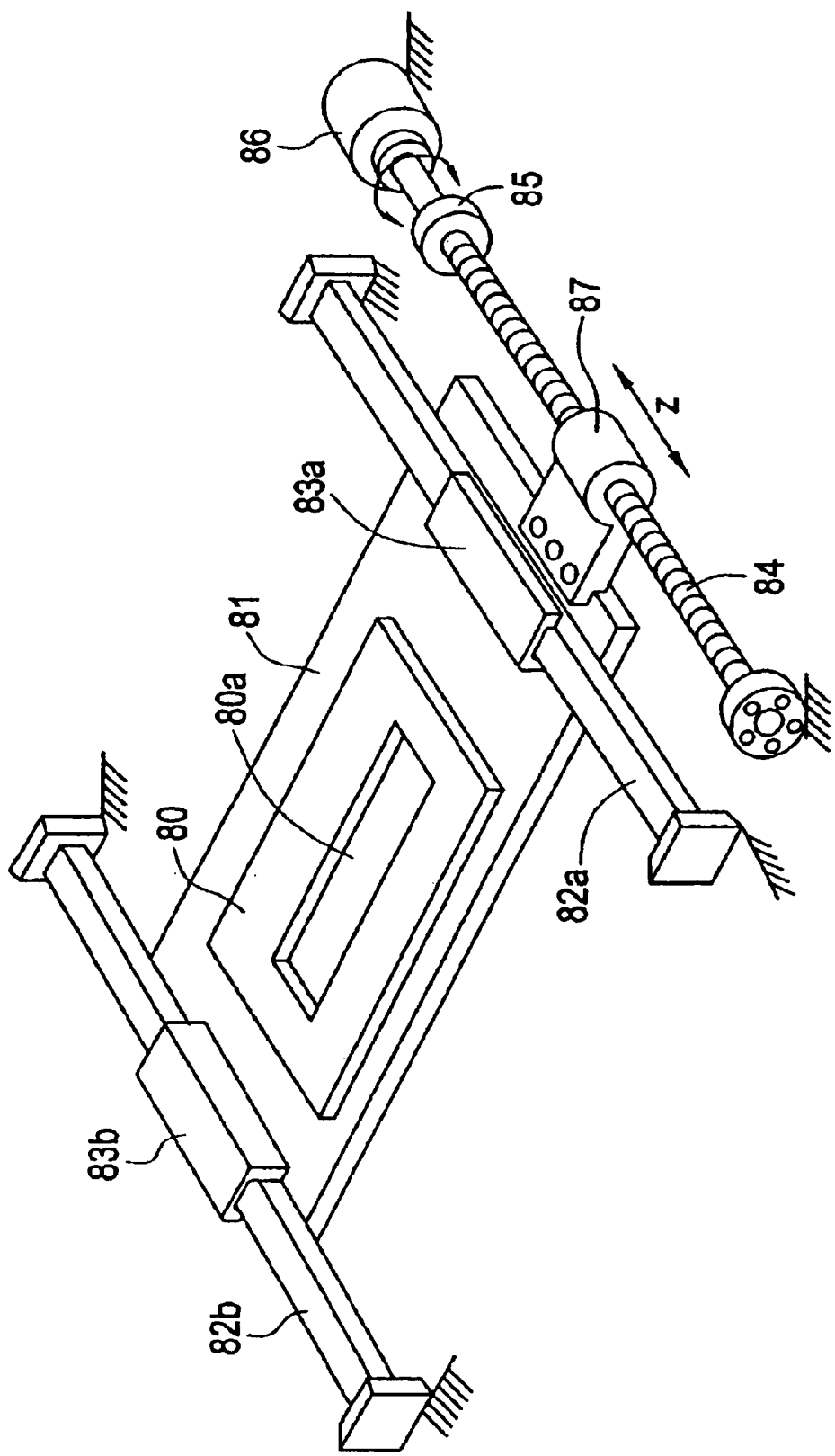
FIG. 8 is a view for explaining a conventional aperture position adjusting mechanism.

FIG. 6 is a flow chart showing aperture 6 movement control processing following the movement of the focal point of the X-ray tube 4, executed in a scan.

The processing is started in response to an input from the keyboard 57 or the mouse 58 in the operating console 200 indicating a scan start instruction (Step S1). The scan start instruction command is sent with parameters of several kinds of scan conditions prescribed beforehand by the operator at the operating console 200.

First, the aperture 6 is set to a predetermined initial position in the z-axis direction (Step S2). Thereafter, a scan is started by starting rotation of the gantry 3 and driving the X-ray tube 4 (Step S3).

In the next Step S4, the position of the aperture 6 is feedback-controlled during the scan execution. The feedback control is conducted with a target:

$$XA/(XA+XB)=XB/(XA+XB),$$

where XA is an output from the reference channel in the detector row A, and XB is an output from the reference channel in the detector row B. Although what is essential is that the control is effected so that XA and XB are equalized, since the values of XA and XB corresponding to an X-ray exposure depend upon the region to be diagnosed, etc., the proportions of outputs of the reference channels in the detector rows to the total output of the reference channels (XA+XB) are employed here so that the target value for the feedback control is constant.

In Step S5, a check is made as to whether the scan is completed, and when the scan is to be continued, the process goes back to Step S4 to continue the processing. When the scan is determined to be completed at Step S5, the processing is terminated.

As described above, a mechanism for performing position control of the aperture 6 in the z-axis direction in the embodiment of the present invention is constructed to comprise:

a pair of rails 21a and 21b disposed along the z-axis direction for slidably mounting the aperture 6;

a large-diameter shaft 23 serving as a first shaft that is hollow and is provided with a bore 23a passing in parallel with a center axis of the large-diameter shaft 23 at a position offset from the center axis;

a small-diameter shaft 25 serving as a second shaft that is received and is rotatably supported within the bore 23a of the large-diameter 23; and a position control motor 7 serving as driving means for rotating the small-diameter shaft 25 in reciprocal directions around an eccentric axis offset from a center axis of the small-diameter shaft 25.

By such a structure, the aperture 6 is moved along the rails 21a and 21b as the small-diameter shaft 25 is eccentrically rotated by the position control motor 7 and, following the eccentric rotation and in a direction opposite to that of the rotation, the large-diameter shaft 23 is eccentrically rotated around the center axis of the bore 23a.

By such a configuration, the mechanism itself can be reduced in size, and besides, play can be reduced and rigidity can be improved. Moreover, the aforementioned structure can be manufactured from a relatively small number of components by relatively simple processing, and can be embodied with low cost.

Many widely different embodiments of the invention may be configured without departing from the spirit and the scope of the present invention. It should be understood that the present invention is not limited to the specific embodiments described in the specification, except as defined in the appended claims.

What is claimed is:

1. An aperture position adjusting mechanism in an X-ray CT system capable of adjusting the position of an aperture, comprising:

a pair of rails disposed along a direction in which said aperture is to be adjusted, for slidably mounting said aperture, said aperture having an aperture opening for limiting an X-ray irradiation range;

a first shaft that is hollow and is provided with a bore passing in parallel with a center axis of said first shaft at a position offset from said center axis, said first shaft being rotatably supported by a base portion of said aperture orthogonally to said pair of rails;

a second shaft that is received and is rotatably supported within said bore of said first shaft; and a driving device for rotating said second shaft in reciprocal directions around an eccentric axis offset from a center axis of said second shaft, said mechanism characterized in that:

said aperture is moved along said rails as said second shaft is eccentrically rotated by said driving device and, following said eccentric rotation and in a direction opposite to that of said rotation, said first shaft is eccentrically rotated around the center axis of said bore.

2. A gantry apparatus in an X-ray CT system, comprising the aperture position adjusting mechanism as defined by claim 1.

3. The gantry apparatus as defined by claim 2, comprising an X-ray detecting device in which a plurality of detector rows are arranged in a carrying direction of a table for carrying a subject, each of said detector rows having a group of detector elements arranged in a direction orthogonal to said carrying direction.

4. The gantry apparatus as defined by claim 3, wherein the direction in which said aperture is to be adjusted coincides with said carrying direction.

5. The gantry apparatus as defined by claim 4, further comprising a control device for feedback-controlling said driving device so that outputs from detector elements at a predefined position in said detector rows are equalized when the focal position of an X-ray source shifts.

6. A method of controlling a gantry apparatus in an X-ray CT system comprising: a gantry rotating device for integrally rotating an X-ray detecting device and an X-ray source, said X-ray detecting device comprising a plurality of detector rows arranged in a carrying direction of a table for carrying a subject, each of said detector rows having a group of detector elements arranged in a direction orthogonal to said carrying direction, said X-ray source disposed at a position opposite to said X-ray detecting device across a cavity portion for inserting said table; an aperture having an aperture opening for limiting an irradiation range of X-rays from said X-ray source; and adjusting device for adjusting the position of said aperture in said carrying direction, said adjusting device comprising:

a pair of rails disposed along a direction in which said aperture is to be adjusted, for slidably mounting said aperture;

a first shaft that is hollow and is provided with a bore passing in parallel with a center axis of said first shaft at a position offset from said center axis, said first shaft being rotatably supported by a base portion of said aperture orthogonally to said pair of rails;

a second shaft that is received and is rotatably supported within said bore of said first shaft; and a driving device for rotating said second shaft in reciprocal directions around an eccentric axis offset from a center axis of said second shaft, said method comprising the steps of:

performing a scan for collecting X-ray projection data of the subject during a rotation of said gantry rotating device; and feedback-controlling said driving device so that outputs from detector elements at a predefined position in said detector rows are equalized when the focal position of the X-ray source shifts during the rotation of said gantry rotating device.

* * * * *